United States Patent [19]

Takahashi et al.

[11] Patent Number: 5,037,612
[45] Date of Patent: Aug. 6, 1991

[54] METHOD AND APPARATUS FOR ANALYZING FLUID SAMPLE

[75] Inventors: Katsuaki Takahashi; Takehide Satou; Tetsuaki Abe, all of Katsuta, Japan

[73] Assignee: Hitachi, Ltd., Tokyo, Japan

[21] Appl. No.: 435,276

[22] Filed: Oct. 19, 1982

[30] Foreign Application Priority Data

Oct. 21, 1981 [JP] Japan ................................ 56-167126

[51] Int. Cl.[5] ............................................ G01N 35/04
[52] U.S. Cl. ...................................... 422/64; 422/67; 436/49
[58] Field of Search ....................... 422/63, 64, 67, 73; 436/49

[56] References Cited

U.S. PATENT DOCUMENTS

| | | | |
|---|---|---|---|
| 4,158,545 | 6/1979 | Yamashita et al. | 422/67 |
| 4,200,607 | 4/1980 | Suzuki | 422/64 |
| 4,305,723 | 12/1981 | Kolber et al. | 422/67 |
| 4,311,394 | 1/1982 | Manabe | 422/64 |
| 4,313,735 | 2/1982 | Yamashita et al. | 436/47 |
| 4,344,768 | 8/1982 | Parker et al. | 422/100 |

FOREIGN PATENT DOCUMENTS

| | | | |
|---|---|---|---|
| 55-1401154 | 11/1980 | Japan | 422/64 |
| 56-154666 | 11/1981 | Japan | 422/66 |

*Primary Examiner*—Michael S. Marcus

*Attorney, Agent, or Firm*—Antonelli, Terry, Stout & Kraus

[57] ABSTRACT

A row composed of reaction vessels is arranged on a turntable and one unit of sample dispenser mechanism as well as one photometer and a plurality units of reagent feeding mechanism are arranged near the turntable. After a sample is added to one specified reaction vessel, the turntable is rotated by 180° or more and stopped so as to advance the reaction vessel containing said sample by half a revolution plus one cell. During this rotation, approximately half of all the vessels cross the light path of the photometer for the absorbance of fluid in each vessel to be measured.

A reagent is added to the specified reaction vessel at the next stop position after sampling in order to start reaction. The turntable is again rotated and stopped so as to advance the reaction vessel by half a revolution plus one cell. During this rotation, the reaction vessel crosses said light path of the photometer for the absorbance of the reaction fluid to be measured. The reaction vessel stops at the second reaction vessel position beyond the initial sample adding position. During the course of repeated rotations, the specified reaction vessel crosses the light path of said photometer a number of times and is stopped at said sample adding position after it is washed to be ready for further use.

12 Claims, 3 Drawing Sheets

METHOD AND APPARATUS FOR ANALYZING FLUID SAMPLE

The present invention relates to a method and an analyzer for analyzing body fluid such as the blood or urine.

In case of a clinical automatic analyzer of discrete type, the sample reacts on reagents within many reaction vessels. Recently, it is widely put into practice to measure the absorbance of the reaction fluid by applying the direct light to reaction vessels. An example of such analyzers is the clinical analyzer described in the U.S. application Ser. No. 268,353 filed on May 29th, 1981 by the same applicant as that of the present invention. In the clinical analyzer according to that application, reactions and direct measurements for a plurality of analyzing items are conducted within reaction vessels arranged in a row on a turntable. Operation of this analyzer has the following characteristics. After a sample is added to a specified reaction vessel at a specified position, the turntable is rotated by one revolution plus one cell to stop there. Then, after the sample is added to a reaction vessel next to said specified reaction vessel, the turntable is again rotated by one revolution plus one cell to stop there. In each cycle, all reaction vessels cross the light path of a photometer. When each reaction fluid containing the sample and a reagent crosses the light path, the absorbance of the reaction fluid is measured, facilitating efficient analyzing operation.

Such a method is suitable to the rate assay. However, there is a limit to increasing the number of samples processed per unit time period equivalent to that of a large apparatus of another type. For raising the processing capacity, the measurement accuracy must be disregarded, resulting in an impractical analyzer.

An object of the present invention is to provide a method and apparatus for analyzing a fluid sample wherein the processing capacity can be raised without deteriorating the measurement accuracy.

Another object of the present invention is to provide a multi-item analyzing apparatus requiring only one unit of sampling mechanism and one photometer.

Still another object of the present invention is to provide a fluid sample analyzing method and apparatus wherein the high measurement accuracy can be attained by ensuring a sufficient light application time for each reaction vessel.

In accordance with the present invention, a number of reaction vessels arranged in an endless row are moved to one direction, a sample is added to a specified reaction vessel concurrently with application of a reagent to another reaction vessel while the row composed of the reaction vessels is stopping, the row stops a few times until it stops after making nearly one revolution, and a plurality of reaction vessels cross the light path of a photometer during movement of the row composed of reaction vessels.

The present invention will be apparent from the following detailed description taken in conjunction with the accompanying drawings, in which.

Figure 1:
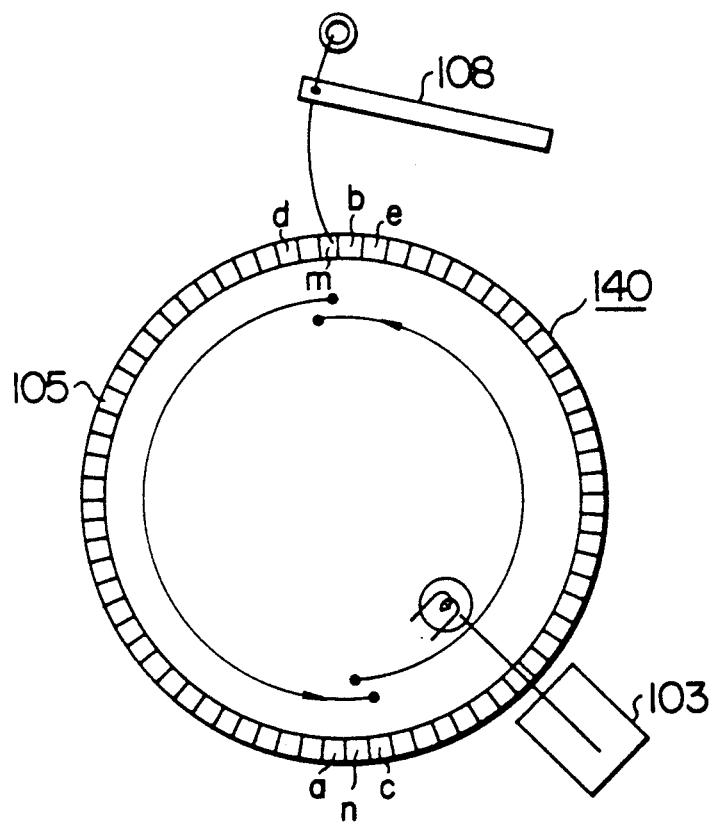
FIG. 1 is a drawing for illustrating the constitution of the analyzing apparatus in accordance with the present invention.

Referring to FIG. 1, the concept of the present invention will hereafter be described. A number of reaction vessels 105 are arranged on the periphery of a turntable 140. These reaction vessels can be divided into the left half group of vessels ranging from position m to position a and the right half group of vessels ranging from position n to position b. At the position m, a sample is added to one specified reaction vessel through a sampling nozzle which is hung down on a dispenser arm 108. Thereafter, the turntable 140 is rotated counterclockwise so that the above described reaction vessel which has been placed at position m may move to the position c. In other words, the turntable 140 is moved by a distance corresponding to half a revolution plus one vessel. Due to the rotation, a reaction vessel which was placed at position a prior to the rotation is moved to the sample adding position m. A reagent is added to the specified reaction vessel placed at the position c.

After a next sample is added to a reaction vessel which is placed at the position m, the turntable is rotated counterclockwise by a distance corresponding to half a revolution plus one vessel. Accordingly, the specified reaction vessel which has been placed at the position c is moved to the position d to stop there. By this rotation, the above described specified reaction vessel crosses the light path of the photometer 103 together with the preceding and succeeding reaction vessels so that the absorbance of the reaction fluid within each of those vessels may be measured.

In the embodiment of FIG. 1, only one unit of sampling mechanism and one photometer are provided. It is not preferable to provide a plurality of units of sampling mechanism because of possible difference among the dispensed sample quantities. A plurality of photometers bring about the difficulty in matching their characteristics.

For further clarifying the effect owing to the present invention, an example wherein the present invention is not applied will be described referring to FIG. 1. That is to say, the operation principle of the analyzing apparatus described in the application Ser. No. 268,353 will be described. After a sample is added to a reaction vessel at position m, the turntable 140 rotates by a distance corresponding to one revolution plus one vessel to stop at the next position beyond the position m. During the rotation period, all of the reaction vessels cross the light path. If the number of vessels arranged on one turntable is increased to, say, 50 or more in order to increase the processing rate per unit time period under the condition that the sampling time interval is kept the same as that for lesser number of vessels, say, 20 vessels, the speed for each reaction vessel on the turntable must be raised. This means that the time period during which each reaction vessel stays within the light path of the photometer is shortened. The output of the photometer is amplified and undergoes analog-digital conversion. If a reaction vessel instantaneously crosses the light path, the noise might often occur in the analog output waveform. Further, the flat portion duration of the output waveform is reduced. Therefore, the measured values for the absorbance of a reaction fluid might be varied.

In accordance with the present invention, the integration time in A-D conversion can be prolonged so that undulation and noise in the waveform may be averaged. As a result, measurement data with fine reproducibility can be obtained.

In the embodiment as shown in FIG. 1, the specified vessel is advanced by a distance corresponding to half a revolution plus one vessel. The present invention is not limited to this embodiment. In FIG. 1, there are two groups of vessels and the turntable stops twice in total during nearly one revolution. It is also possible to adopt a method wherein three groups or more of vessels are provided and turntable stops as many times as the number of groups during nearly one revolution. Further, in the embodiment of FIG. 1, the specified vessel is displaced by one vessel position per revolution. The displacement may be chosen to be a plurality of vessel positions. The present invention may also be applied to a case wherein the displacement distance caused by rotating operation is less than the number of vessels contained in a group of vessels. In FIG. 1, for example a reaction vessel placed at the sampling position m is displaced to a reagent adding position a to stop there. The specified reaction vessel is placed at the position e which is one vessel on this side of the position b by the succeeding rotating operation. By repeating such rotation which corresponds to half a revolution minus one vessel, a vessel to which a sample is to be added and another vessel to which a reagent is to be added can be successively changed.

Figure 2:
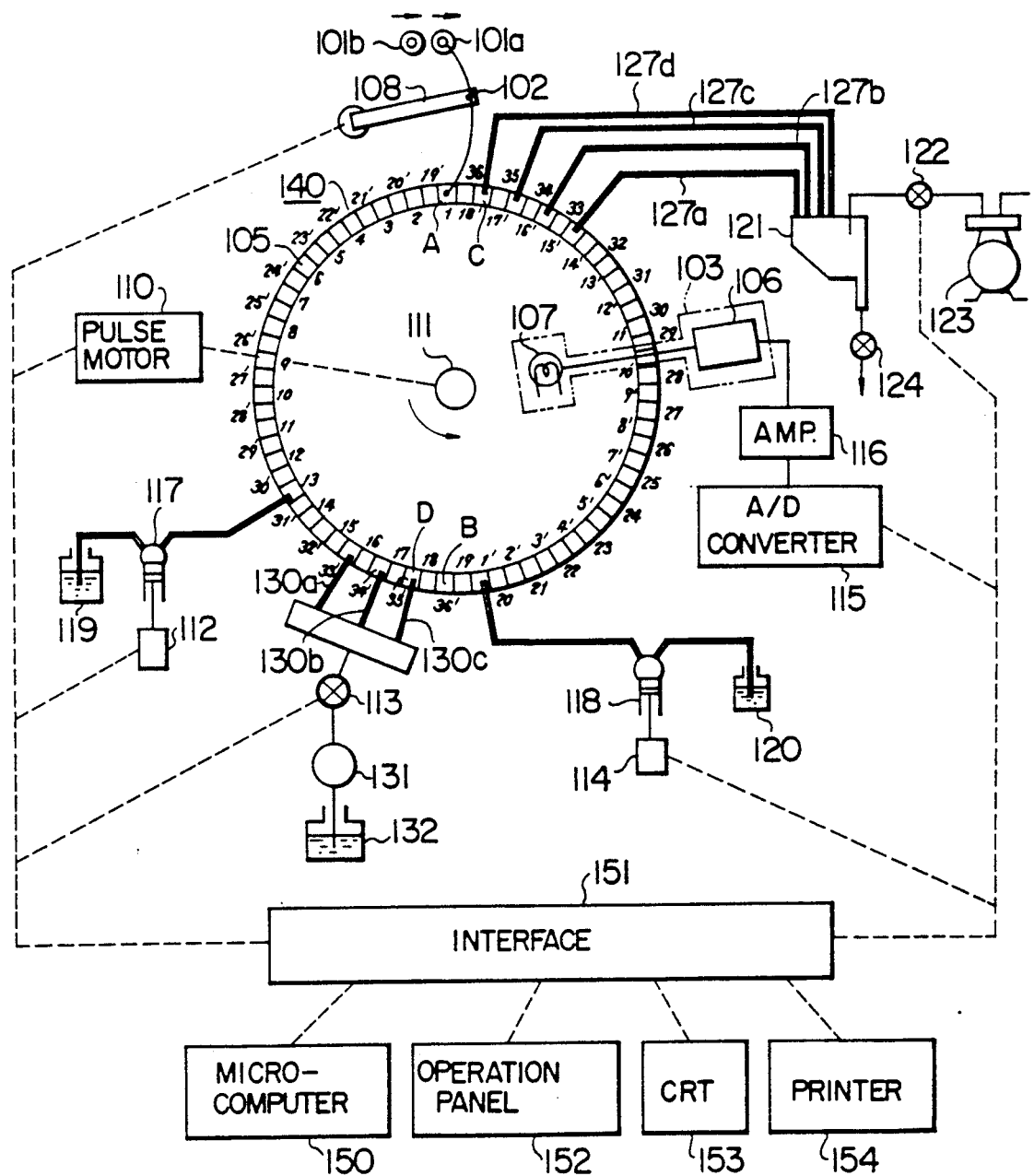
FIG. 2 shows the rough constitution of an embodiment of the present invention.

FIG. 2 shows an embodiment wherein the present invention has been applied to a multi-item clinical analyzer. Displacement is carried out so that sample cups 101 containing blood samples respectively for a plurality of analyzing items may be successively positioned. A turntable 140 can be rotated around the rotation axis 111. On the turntable 140, 72 or an even number of square-shaped reaction cells 105 made of glass are arranged to form an endless row of vessels. The reaction cells located every other cell counterclockwise are designated as the positions 1 to 36 as shown in FIG. 2, and the reaction cells located every other cell counterclockwise starting from the cell between positions 19 and 20 are designated as positions 1' to 36'.

A sample dispenser arm 108 is so arranged as to inject a sample 101 into a reaction cell 105 placed at a sampling position 1 through a sampling nozzle 102 hanging on the dispenser arm 108 during the double reciprocation of the arm. A dispenser 118 is so arranged as to inject a first reagent from a reagent tank 120 into a reaction cell 105 placed at a position 1'. A dispenser 117 is so arranged as to inject a second reagent from a reagent tank 119 into a reaction cell placed at a position 13. Above reaction cells placed at positions 33', 34' and 35', washing fluid discharge nozzles 130a, 130b and 130c are placed and these nozzles are connected to a pump 131 via a valve 113. The pump 131 feeds washing fluid from a washing fluid tank 132. In addition, at positions 33, 34, 35 and 36, there provided fluid suction nozzles 127a, 127b, 127c and 127d connected to a suction bottle 121. The suction bottle 121 is connected to a vacuum pump 123 through a valve 122. The fluid sucked by the fluid suction nozzles 127a to 127d is put in the suction bottle 121 and exhausted through a valve 124. The fluid discharge nozzles 130a to 130c are placed opposite to the fluid suction nozzles 127a to 127d with the axis 111 between.

A photometer 103 is fixed around the turntable 140. The photometer 103 is composed of a light source 107 and a spectroscope 106. The light path from the light source 107 passes through a position 10' to arrive at the spectroscope 106 comprising a concave grating which functions as a dispersant and a plurality of light detectors each of which receives a monochromatic light after dispersion of the multi-wavelength light. Every time a reaction cell is placed at the position 10', the photometer 103 electrically selects a monochromatic light corresponding to the reaction fluid contained within that reaction cell. The monochromatic light signal thus selected is passed through an amplifier 116 and is converted into a digital signal by an analog-digital converter 115. The digital signal is led through an interface 151 to a microcomputer 150, in which required operations are performed and the result thereof is stored in a memory. When a plurality of photometric operations for a specified analyzing item are all completed, the plurality of photometric data are compared with each other and required calculations are made to print out a concentration value with respect to the analyzing item by a printer 154. The measurement result may be displayed on a CRT 153.

The microcomputer 150 also controls operations of the dispenser arm 108 for carrying a sampling nozzle 102, a pulse motor 110 for rotating the turntable 140 by a specified angle, a driving source 112 for the dispenser 117, the opening and shutting valve 113 for feeding the washing fluid, a driving source 114 for the dispenser 118, and the vacuum discharge valve 122.

Operation of the clinical analyzer thus constructed will be described hereafter.

Figure 3:
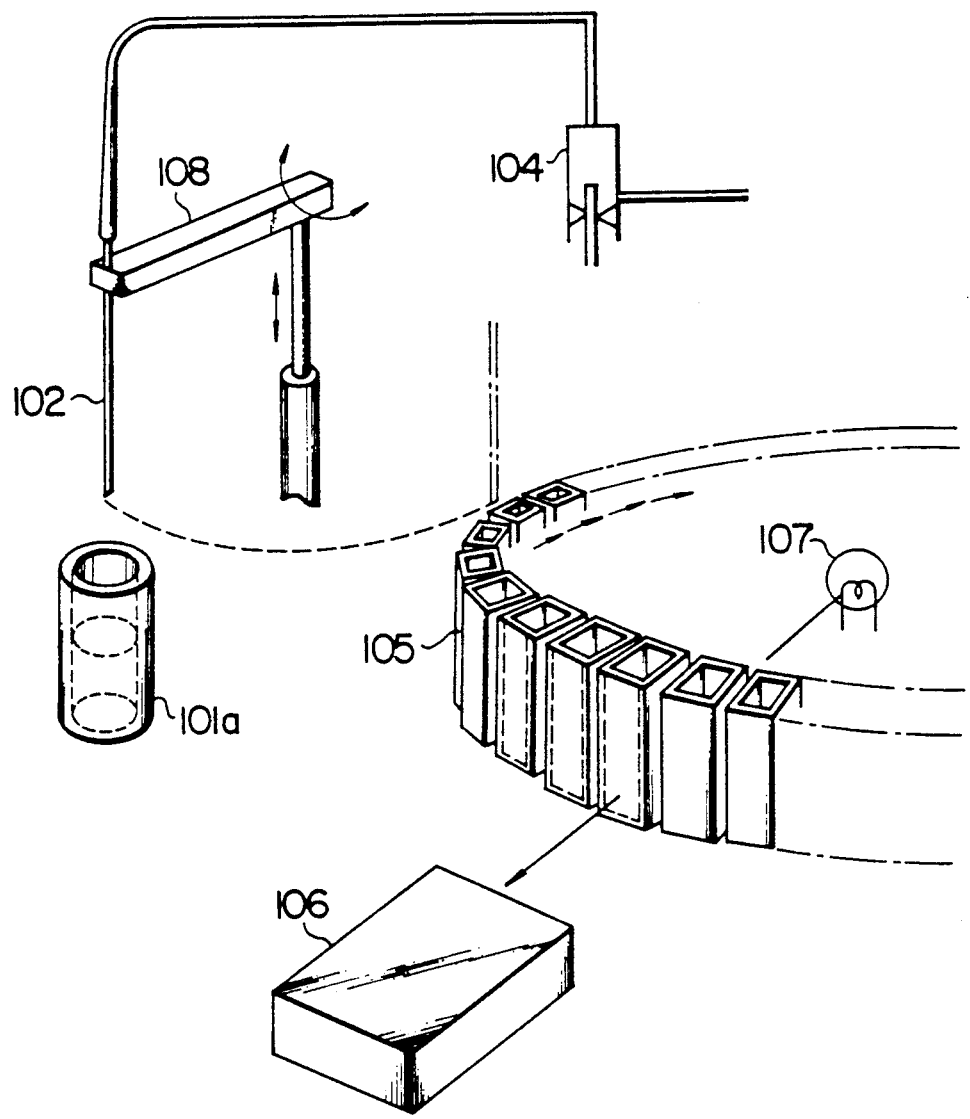
FIG. 3 is a drawing for illustrating how a sampling probe operates.

By pressing a start button on an operation panel 152 as shown in FIG. 2, a sample cup 101a is placed at a sucking position and the dispenser arm 108 is actuated. On the other hand, the turntable 140 is rotated and stopped so as to place a reaction cell A at the sampling position 1. As shown in FIG. 3, the dispenser arm 108 which holds the sampling nozzle 102 falls down to insert the tip of the nozzle 102 into the sample fluid within the sample cup 101a. A specified quantity of sample is sucked and held in the nozzle 102 by sucking operation caused by a microsyringe 104. After the nozzle 102 is pulled up, it is placed above the position 1 by rotation of the dispenser arm 108. The nozzle 102 falls down to discharge the sample held therein into the reaction vessel A. After the dispensation, the row composed of reaction cells is rotated by an angle corresponding to half a revolution plus one cell. As a result, the reaction cell A is displaced to the position 1', a reaction cell B which was placed at the position 36' is displaced to the position 1, and a reaction cell C which was placed at the position 36 is displaced to the position 36'. That is to say, the turntable is rotated by an angle corresponding to 37 cells. This number must be an odd number which is not less than 3. A first reagent is applied to the reaction cell A which was been displaced to the reagent adding position 1', reaction between the sample and the first reagent being started. The sample for another analyzing item is applied from the sample cup 101a to the reaction cell B which has been displaced to the sampling position 1.

Thereafter, the turntable 140 is rotated by a distance corresponding to half a revolution plus one cell and is stopped. In case the sample cup 101a is used for measurement of only two analyzing items, a sample cup 101b is placed at the sucking position concurrently with rotation of the turntable 140. In consequence of repetition of such operation, the sample is dispensed to reaction cells in sequence of A, B, C, D and so on. Namely, the sample is dispensed to reaction cells located at intervals of 180° plus one cell and the sample is dispensed to every other cell.

Paying attention to only the reaction cell A which was placed at the position 1 before, the position at which the reaction cell A stops in each cycle and the analysis processes it undergoes will be hereafter described.

The reaction cell which has been subjected to sample dispensation at the position 1 is displaced to the position 1' in next half cycle and fed with the first reagent by the reagent dispenser 118. After reagent dispensation is completed, the reaction cell A is rotated counterclockwise and stopped at the position 2. During this rotation, the reaction cell A crosses the light path of the light source 107, the absorbance being measured by the photometer 103. With the advance of cycles, the reaction cell A successively stops at positions 2', 3, 3', 4, 4' and so on. When the reaction cell A stops at the position 13, it is fed with the second reagent by the reagent dispenser 117. The absorbance of the reaction cell A with reaction in progress caused by addition of the first or second reagent is measured every time the reaction cell A crosses the light path, as described before. After repetition of rotation by an angle corresponding to half a revolution plus one cell and stopping, the reaction cell stops at the position 33. At this position, the fluid suction nozzle 127a is inserted into the reaction cell A and the valve 122 is opened so as to suck the reaction fluid within the cell A into the suction bottle 121 by the vacuum pump 123.

In the next half cycle, the reaction cell A stops at the position 33'. At this position, the cell washing fluid discharge nozzle 130a is inserted into the reaction cell A and the valve 113 is opened to inject water from the pump 131 into the cell for washing. At the position 34 in further next half cycle, the washing water is sucked by the nozzle 127b. After such operation is repeated three times, an empty reaction cell which has been completely cleaned is obtained at the position 36. The reaction cell A returns to the position 1 to be ready for further use.

Figure 4:
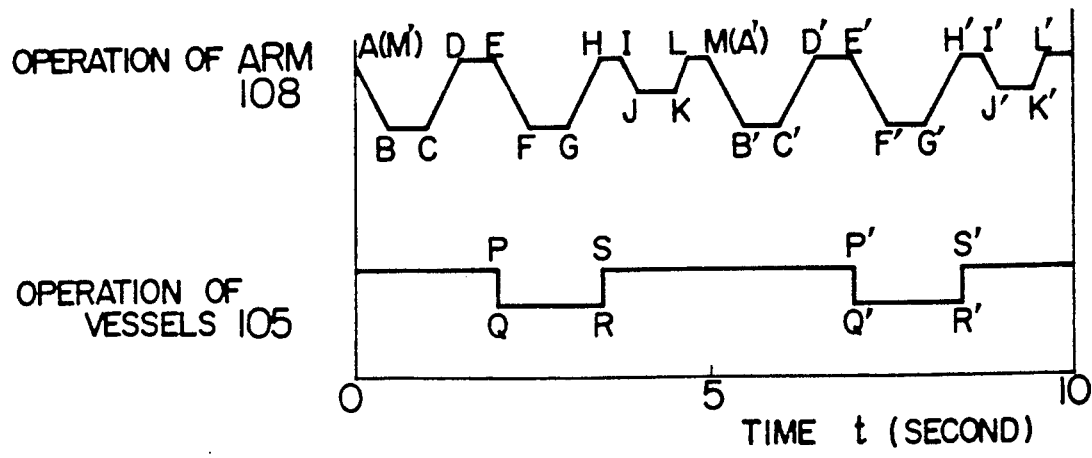
FIG. 4 is a drawing for illustrating how a dispenser arm and a row of reaction vessels operate.

The above described operation is carried out in accordance with a time chart as shown in FIG. 4. In FIG. 4, the time period for one cycle is 10 seconds. The upper curves A to M and A' to M' show the movement of the dispenser arm 108. The lower curve shows the movement of the reaction cell row. In the movement of the dispenser arm 108, lines AB and A'B' represent insertion of the probe 102 into the sample cup 101, lines BC and B'C' represent suction of the sample, lines CD and C'D' represent the rise of the probe 102, lines DE and D'E' represent the rotational movement of the dispenser arm 108, lines EF and E'F' represent the descent of the probe 102 toward a reaction cell, lines FG and F'G' represent the discharge of the sample, lines GH and G'H' represent the rise of the probe 102, lines HI and H'I' represent the movement of the probe 102 toward a probe washing tank which is not illustrated, curved lines IJKL and I'J'K'L' represent the washing operation of the inner wall as well as the outer wall of the probe 102 in the probe washing tank, and lines LM and L'M' represent the movement for returning to the sample.

The row composed of the vessels 105 is stopped during periods represented by lines QR and Q'R' and is rotated during periods represented by lines SP' and S'P. During periods SP' and S'P respectively lasting for 3.5 seconds, it is possible to measure the absorbance of fluids within 37 reaction cells corresponding to half a revolution plus one cell. During a period from the dispensation completion H in the first reciprocation of the dispenser arm 108 until the dispensation start E' in the second reciprocation as described in FIG. 4, the row composed of reaction cells is rotated by half a revolution plus one cell. The reaction cell row substantially advances by a distance corresponding to one revolution plus two cells in one cycle of 10 seconds.

We claim:

1. A fluid sample analyzing apparatus comprising:
drive means for moving an endless row composed of a number of reaction vessels so that said row may repeat continuous movement and stopping at specified time intervals along a closed symmetric path of movement thereof, said drive means being controlled so that the distance said reaction vessel row advances between a stop position and the next stop position corresponds to a distance of a plurality of reaction vessels as determined by summing the quotient obtained by dividing the total number of reaction vessels by an integer which is not less than 2 together with an integer of plus 1;
sample adding means disposed at a specified sample adding position along the path of movement of said reaction vessel row and being controlled for adding a sample to a reaction vessel which stops at said specified sample adding position;
reagent adding means disposed at a reagent adding position along the path of movement of said reaction vessel row other than said specified sample adding position and being controlled for adding a reagent to a reaction vessel which stops at said reagent adding position;
photometric means for measuring optical characteristics of fluids within reaction vessels which cross the light path thereof while said reaction vessel row is moving;
waste fluid removing means being controlled for removing waste fluid from the reaction vessel after measurement by said photometric means, said waste fluid removing means being disposed at a fluid removing position along the path of movement of said reaction vessel row between said photometric means and said sample adding means, said waste fluid removing means including a fluid suction and exhausting part;
cleaning fluid adding means being controlled for adding cleaning fluid to the reaction vessel after measurement by said photometric means, said cleaning fluid adding means being disposed at a fluid adding position apart from said fluid removing position along a path of movement of said reaction vessel row between said sample adding means and said reagent adding means, said cleaning fluid adding means including a cleaning fluid discharge part, said cleaning fluid adding means and said waste fluid removing means being located on diametrically opposite sides of the path of movement of said reaction vessel row with the center of rotation of the drive means being located therebetween; and
control means for controlling said drive means, said sample adding means, said reagent adding means, waste fluid removing means and said cleaning fluid adding means so as to enable analyzing of a fluid sample, said control means controlling said drive means to advance said reaction vessel row a distance between a stop position and the next stop position corresponding to a distance of a plurality of reaction vessels as determined by summing the quotient obtained by dividing the total number of reaction vessels by an integer which is not less than 2 together with an integer of plus 1, said control means controlling said sample adding means to add a sample to the reaction vessel which stops at said specified sample adding position, said control means controlling said reagent adding means for adding a reagent to a reaction vessel which stops at said reagent adding position, said control means controlling said waste fluid removing means to remove waste fluid from the reaction vessel after measurement of the reaction vessel by said photometric means, and said control means controlling said cleaning fluid adding means to add cleaning fluid to the reaction vessel after the measurement of the reaction vessel by said photometric means.

2. A fluid sample analyzing apparatus according to claim 1, wherein said drive means includes a turntable.

3. A fluid sample analyzing apparatus according to claim 1, wherein the total number of reaction vessels is an even number, and the advanced distance of said reaction vessel row corresponds to an advancement of an odd number of reaction vessels, the odd number being not less than 3.

4. A fluid sample analyzing apparatus according to claim 1, wherein the integer utilized for obtaining the quotient is an integer of 2, and said photometric means is fixedly disposed at a predetermined position along the path of movement of said reaction vessel row.

5. A fluid sample analyzing apparatus comprising:
drive means for moving an endless row composed of a number of reaction vessels so that said row may repeat continuous movement and stopping at specified time intervals along a closed symmetric path of movement thereof said drive means being controlled so that the distance said reaction vessel row advances between a stop position and the next stop position corresponds to a distance of a plurality of reaction vessels as determined by summing the quotient obtained by dividing the total number of reaction vessels by an integer which is not less than 2 together with an integer of minus 1;

sample adding means disposed at a specified sample adding position along the path of movement of said reaction vessel row and being controlled for adding a sample to a reaction vessel which stops at said specified sample adding position;

reagent adding means disposed at a reagent adding position along the path of movement of said reaction vessel row other than said specified position and being controlled for adding a reagent to a reaction vessel which stops at said reagent adding position;

photometric means for measuring optical characteristics of fluids within reaction vessels which cross the light path thereof while said reaction vessel row is moving;

waste fluid removing means being controlled for removing waste fluid from the reaction vessel after measurement by said photometric means said waste fluid removing means being disposed at a fluid removing position along the path of movement of said reaction vessel row between said photometric means and said sample adding means;

cleaning fluid adding means being controlled for adding cleaning fluid to the reaction vessel after measurement by said photometric means, said cleaning fluid adding means being disposed at a fluid adding position apart from said fluid removing position among the path of movement of said reaction vessel row between said sample adding means and said reagent adding means, said waste fluid removing means and said cleaning fluid adding means being located on diametrically opposite sides of the path of movement of said reaction vessel row; and control means for controlling said drive means, said sample adding means, said reagent adding means, said waste fluid removing means and said cleaning fluid adding means so as to enable analyzing of a fluid sample, said control means controlling said drive means to advance said reaction vessel row a distance between a stop position and the next stop position corresponding to a distance of a plurality of reaction vessels as determined by summing the quotient obtained by dividing the total number of reaction vessels by an integer which is not less than 2 together with an integer of minus 1, said control means controlling said sampling adding means to add a sample to the reaction vessel which stops at said specified sample adding position, said control means controlling said reagent adding means to add a reagent to the reaction vessel which stops at said reagent adding position, said control means controlling said waste fluid removing means to remove waste fluid from the reaction vessel after measurement of the reaction vessel by said photometric means, and said control means controlling said cleaning fluid adding means cleaning fluid to the reaction vessel after measurement of the reaction vessel by said photometric means.

6. A fluid sample analyzing apparatus according to claim 5, wherein the total number of reaction vessels is an even number, and the advanced distance of said reaction vessel row corresponds to an advancement of an odd number of reaction vessels, the odd number being not less than 3.

7. A fluid sample analyzing apparatus according to claim 5, wherein the integer utilized for obtaining the quotient is an integer of 2, and said photometric means is fixedly disposed at a predetermined position along the path of movement of said reaction vessel row.

8. A fluid sample analyzing apparatus comprising:
advancing means for advancing a reaction vessel row composed of a number of reaction vessels arranged in an endless form along a closed symmetric path of advancing movement thereof;

sample adding means disposed at a sample adding position along the path of advancing movement of the reaction vessel row and being controlled for adding a sample to a specified reaction vessel of the reaction vessel row at the sampling adding position while the reaction vessel row is stopped;

said advancing means being controlled so that the reaction vessel row is advanced by a distance corresponding to half a revolution of the endless form of the reaction vessel row plus or minus at least one reaction vessel and stopped;

reagent adding means disposed at a reagent adding position along the path of advancing movement of the reaction vessel row and being controlled for adding a reagent to another reaction vessel of the reaction vessel row at the reagent adding position while the reaction vessel row is stopped;

photometer means arranged so as to have a light path through which a plurality of the reaction vessels within the reaction vessel row cross during advancement of the reaction vessel row for providing a measurement indication;

cleaning liquid adding means being controlled for adding cleaning liquid to a reaction vessel after measurement thereof by said photometer means, said cleaning liquid adding means being disposed at a liquid adding position along the path of advancing movement of the reaction vessel row through which the reaction vessel advances from the sample adding position to the reagent adding position;

waste liquid removing means being controlled for removing waste liquid from the reaction vessel after measurement thereof by said photometer means, said waste liquid removing means being disposed at a liquid removing position away from said liquid adding position along the path of advancing movement of the reaction vessel row through which the reaction vessel advances between the photometer means and the sample adding position, said cleaning liquid adding means and said waste liquid removing means being located on diametrically opposite sides of the path of advancing movement of the reaction vessel row; and control means for controlling said advancing means, said sample adding means, said reagent adding means, said cleaning liquid adding means and said waste liquid removing means so as to enable analyzing of a fluid sample, said control means controlling said advancing means so that the reaction vessel row is advanced by a distance corresponding to half a revolution of the endless form of the reaction vessel row plus or minus at least one reaction vessel and stopped, said control means controlling said sample adding means to add a sample to a specified reaction vessel of the reaction vessel row at the sampling adding position while the reaction vessel row is stopped, said control means controlling said reagent adding means to add a reagent to another reaction vessel of the reaction vessel row at the reagent adding position while the reaction vessel row is stopped, said control means controlling said cleaning liquid adding means to add cleaning liquid to a reaction vessel after measurement of the reaction vessel by said photometer means, and said control means controlling said waste liquid removing means to remove waste liquid from the reaction vessel after measurement of the reaction vessel by said photometer means.

9. A fluid sample analyzing apparatus according to claim 8, wherein said reaction vessel row comprises an even number of reaction vessels, and the advancement distance corresponds to an odd number of reaction vessels, the odd number being at least 3.

10. A fluid sample analyzing apparatus according to claim 8, wherein said photometer means is permanently installed at a specified position.

11. A fluid sample analyzing apparatus according to claim 8, wherein said waste liquid removing means includes a plurality of suction nozzles.

12. A fluid sample analyzing apparatus according to claim 11, wherein said cleaning liquid adding means includes a plurality of discharge nozzles.

* * * * *